United States Patent [19]
Shakinovsky et al.

[11] Patent Number: 5,837,880
[45] Date of Patent: Nov. 17, 1998

[54] COMPACT ULTRASONIC CALIBRATION BLOCK

[75] Inventors: Michael L. Shakinovsky, Southbury; Robert E. Lucas, Brookfield, both of Conn.

[73] Assignee: Sperry Rail Service, Inc., Danbury, Conn.

[21] Appl. No.: 915,401

[22] Filed: Aug. 20, 1997

[51] Int. Cl.⁶ .................................................. G01D 18/00
[52] U.S. Cl. ................................................................. 73/1.86
[58] Field of Search .................................... 73/1.86, 1.78, 73/1.81

[56] References Cited

U.S. PATENT DOCUMENTS

| | | | |
|---|---|---|---|
| 3,933,026 | 1/1976 | Ham et al. | 73/1.86 |
| 4,466,270 | 8/1984 | Kimura et al. | 73/1.86 |
| 5,163,027 | 11/1992 | Miller et al. | 73/1.86 |
| 5,501,096 | 3/1996 | Stettner et al. | 73/1.79 |

*Primary Examiner*—Robert Raevis
*Attorney, Agent, or Firm*—Francis N. Carten

[57] ABSTRACT

An ultrasonic test standard is formed by a metal block having a unique shape incorporating an arcuate surface and a series of reflectors that enable discreet instrument measurement verifications in a relatively small area. This calibration block, though relatively small and light in weight, will perform all of the functions of a standard IIW (International Institute of Welding) type block and additional functions.

9 Claims, 2 Drawing Sheets

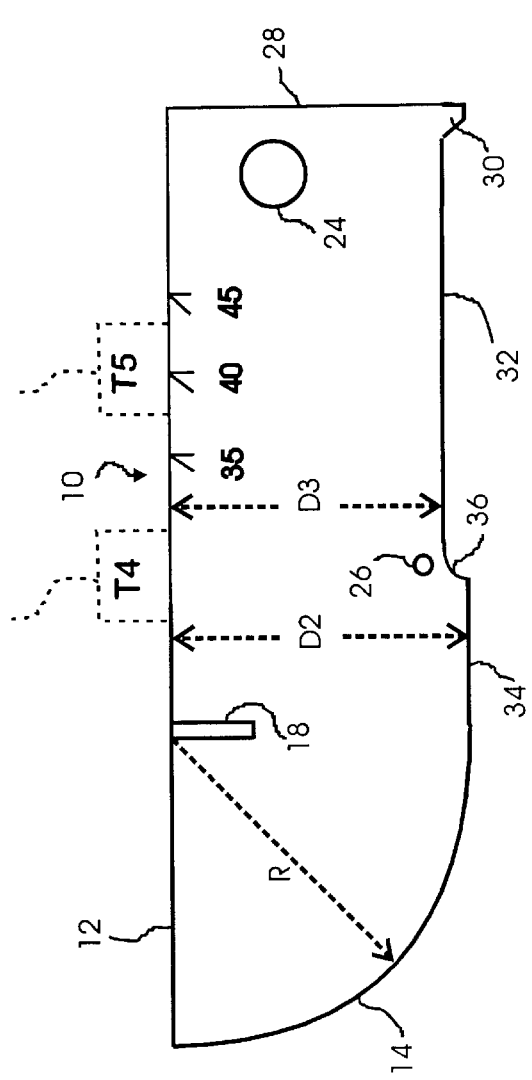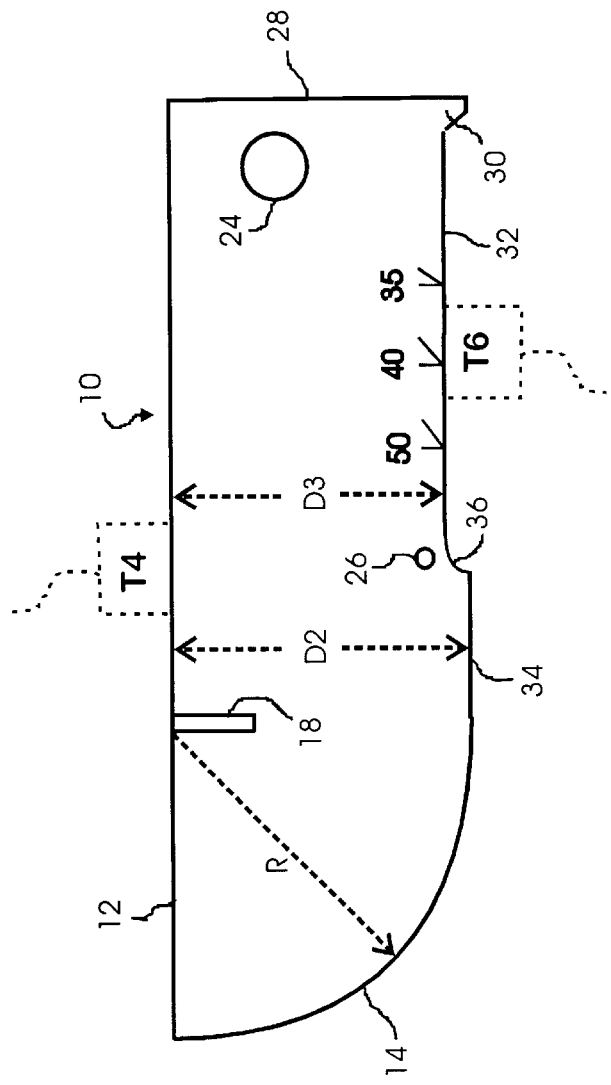

COMPACT ULTRASONIC CALIBRATION BLOCK

BACKGROUND OF THE INVENTION

In the past, ultrasonic test standards have taken the form of a relatively large metal calibration block, e.g., the IIW (International Institute of Welding) type block. Portability of such calibration blocks has been impaired by their size and weight. The goal of the present invention is to provide a calibration block of reduced size and weight that will perform all of the functions of a standard type block, and additional functions as well.

SUMMARY OF THE INVENTION

The present invention is embodied in and carried out by an ultrasonic calibration block having a unique shape that enables discreet instrument measurement verifications in a relatively small area. The calibration block comprises a rigid section of material that contains a radius and a plurality of ultrasonic reflectors that are used for various calibration exercises. The calibration block is used in the calibration of ultrasonic instrumentation designed for the purposes of flaw detection, or thickness measurement, or for calibration of the instrumentation for any other test within the capabilities of the instrumentation, or verification of the performance of the instrumentation. The calibration block can also be used for time/distance measurements when verification of calibration is required. The calibration block can be used for contact or immersion ultrasonic tests, trials or verifications. Specifically, the calibration block enables repeat signals from the radius; provides an actual two-inch (2") dimension; is lighter and easier to carry, weighing only three (3) pounds; enables one-inch (1") $V_s$ screen calibration using a zero-degree longitudinal wave (0°) transducer; and provides for ultrasonic system resolution check. The known tests that can be conducted using this invention are as follows:
Screen Height Linearity
Vertical Linearity
Calibration for Longitudinal Wave linearity
Calibration with repeat signals for Shear Wave Linearity using Angle beam search unit
Calibration for Shear Wave Linearity using Longitudinal Wave Search Unit
Calibration for Rayleigh Wave Linearity
Search Unit energy exit point location
Search Unit angle verification
System Resolution check
Near surface resolution check
Reference sensitivity setup
Instrument calibration in inches
Instrument calibration in microseconds

DESCRIPTION OF THE DRAWINGS

The written description of the present invention will be more fully understood when read with reference to the accompanying drawings, of which:

FIG. 4 is a second side view of the calibration block shown in FIG. 1.

FIG. 5 is a second side view of an alternate version of the calibration block shown in FIG. 1.

DETAILED DESCRIPTION OF THE PREFERRED EMBODIMENT

Figure 3:
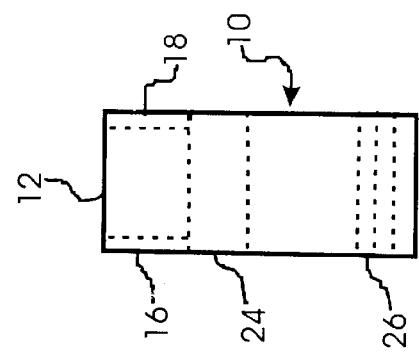
FIG. 3 is an end view of the calibration block shown in FIG. 1.
Figure 2:
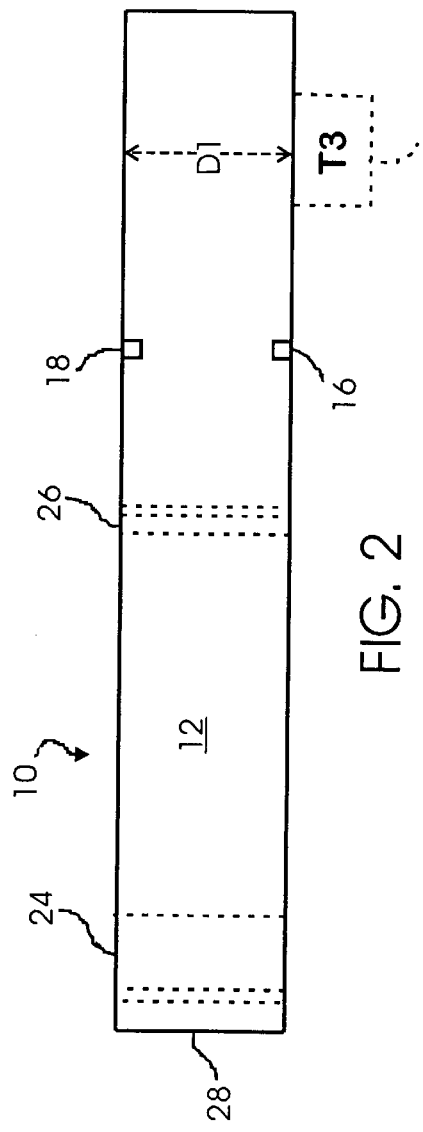
FIG. 2 is a top view of the calibration block shown in FIG. 1.
Figure 1:
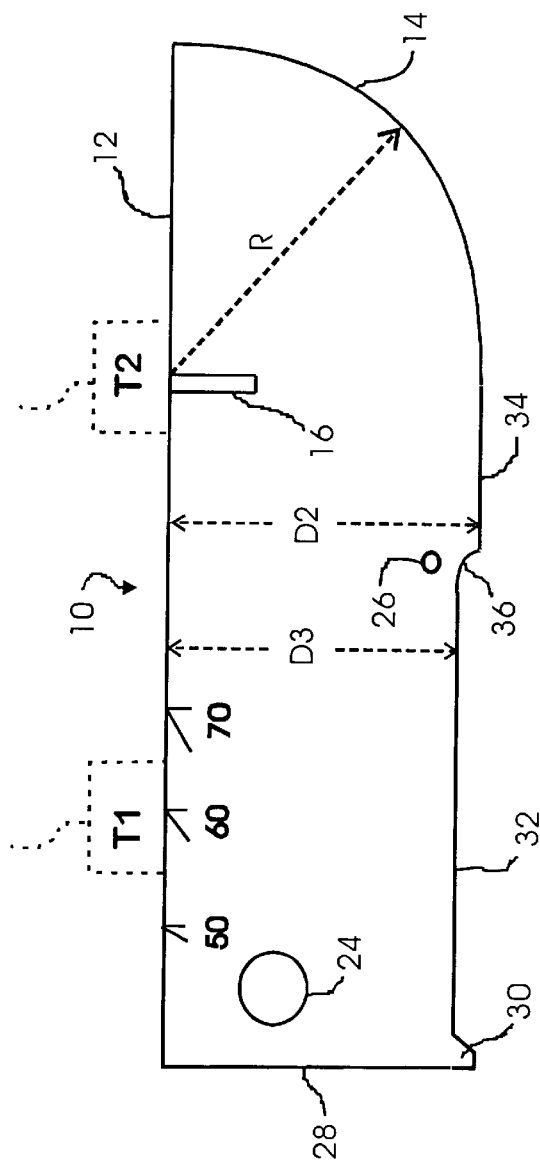
FIG. 1 is a first side view of the calibration block forming the ultrasonic test standard.

Referring now specifically to FIGS. 1, 2, 3, 4 and 5, the calibration block 10 forming the ultrasonic test standard is fabricated from ultrasonically tested carbon steel, stainless steel, or other required material. In instances where other material is used, certain dimensions can change to accommodate velocity and angle changes. The calibration block 10 comprises a rigid section of the selected material, and comprises a radius and a plurality of ultrasonic reflectors that are used for various calibration exercises. The fabrication of this calibration block 10 is accomplished by machining the outer surfaces, drilling the larger and smaller holes through the thickness dimension of the calibration block, surface grinding of the opposed surfaces, and engraving indicia of a series of stations for measurements of the units to be tested. The flat top surface 12 is the transducer scanning surface used to interrogate the arcuate surface 14 having a two (2") inch radius R for angle beam calibration (either transverse or longitudinal wave). For these tests, a transducer T2 is positioned as shown in FIG. 1. The thickness dimension D1 shown in FIG. 2 allows for a one (1") inch (and multiples thereof) thickness calibration using a transducer T3 as shown in FIG. 2. The laterally-opposed notches 16 and 18 serve to reflect the sound from the arcuate surface 14 back to the arcuate surface 14, thus causing multiple two (2") inch sound path reflections from the arcuate surface 14. The top flat surface 12 is also used to interrogate the reflector holes 24 and 26 in order to establish beam angle measurement as the transducer T1 is aligned with a selected one of the engraved test positions marked with the beam angles for which the transducer T1 is being tested, i.e., 50, 60 or 70 degrees to the larger reflector hole 24 as shown in FIG. 1. On the opposite side of the calibration block 10 shown in FIG. 4, the transducer T5 is aligned with a selected one of the engraved test positions marked with the beam angles 35, 40 or 45 degrees to the smaller reflector hole 26. The notches 16 and 18 also serve as an index point or beam exit reference position for use during the beam angle measurement procedure. Dimension D2 (FIGS. 1,4 & 5) is equal to radius R, and allows for two (2") inch longitudinal calibration thickness from either the top surface 12 or the bottom surface 34. Dimension D3 (FIGS. 1,4 & 5) is equivalent to one (1") inch of material velocity in the transverse mode as the energy reflects from either the top surface 12 or the bottom surface segment 32. The leg 30 is to provide the flat end 28 with a vertical dimension equal to dimension D2, and thereby prevent wobbling when the calibration block 10 is rested on bottom surface 34. The arcuate curved surface 36 is a transition radius between the parallel bottom surface segments 32 and 34.

In a carbon steel calibration block 10, the distance from the upper surface of the small hole 26 to the bottom flat segment 34 is traversed by an ultrasonic pulse in one (1 μsec.) microsecond; the distance from the top surface 12 to the top of the large hole 24 is traversed by an ultrasonic pulse in two (2 μsec.) microseconds; and the distance from the vertical flat end surface 28 to the large hole 24 is traversed by an ultrasonic pulse in one (1 μsec.) microsecond. Bottom surface segments 32 and 34 and the top of the hole 26 present three reflective surfaces to the sound energy from a transducer T4 (FIGS. 4 and 5) positioned on surface 12 above the hole 26, thereby allowing for a check of transducer/system resolution.

In the alternative version of the calibration block 10 shown in FIG. 5, the flat bottom surface 32 is also used to interrogate the large reflector hole 24 in order to establish beam angle measurement as a transducer T6 is aligned with a selected one of the engraved test positions marked with the beam angles for which the transducer T6 is being tested, i.e., 35, 40 or 50 degrees. When the calibration block 16 is used in this manner, it may conveniently be rested on the flat surface 12.

Certain modifications and variations of the disclosed embodiments of the present invention will be apparent to those skilled in the art. For example, the various dimensions of the calibration block can be altered according to the material from which it is fabricated so as to accommodate different sound velocity values. Also, the thickness dimension D1 will also change according to the requirements of the application for which the block is intended. The calibration block can be fabricated in metric or imperial dimensions. It should be understood that the disclosed embodiment is intended to be illustrative only, and not in any way restrictive of the scope of the invention as defined by the claims set forth hereunder.

We claim:

1. An ultrasonic test block comprising:

(a) a flat top surface;

(b) first and second parallel flat side surfaces having a predetermined distance therebetween;

(c) a flat end and an arcuate end;

(d) opposed notches formed in said first and second parallel flat side surfaces at the base of the radius defining said arcuate end;

(e) a bottom surface comprising (i) a first flat bottom segment extending from said flat end, (ii) a second flat bottom segment extending from said arcuate end, and a curved portion joining said first flat bottom segment and said second flat bottom segment, said first and second flat bottom segments being parallel to said flat top surface;

(f) a first hole extending between said first and second parallel flat side surfaces perpendicularly thereto;

(g) a second hole extending between said first and second parallel flat side surfaces and parallel to said first hole, and positioned in proximity to said curved portion between said first flat bottom segment and said second flat bottom segment; and (h) a plurality of sets of indicia on each of said first and second parallel flat side surfaces to aid in measuring an ultrasonic test head.

2. The ultrasonic test block of claim 1, wherein first and second sets of indicia are formed on each of said first and second parallel flat side surfaces, respectively, immediately adjacent said flat top surface.

3. The ultrasonic test block of claim 1, wherein first and second sets of indicia are formed on each of said first and second parallel flat side surfaces, respectively, said first set of indicia being immediately adjacent said flat top surface and said second set of indicia being immediately adjacent said first flat bottom segment.

4. The ultrasonic test block of claim 2 or 3, wherein each of said sets of indicia comprises a plurality of engraved test positions, each test position being marked with the beam angle for which a transducer can be tested at that test position.

5. The ultrasonic test block of claim 4, wherein the beam angle marked at each test position is measured to one of said first and second holes.

6. The ultrasonic test block of claim 2 or 3, wherein said first hole is positioned so that the distance from said top surface to the top of said first hole is traversed by an ultrasonic pulse in two (b 2$\mu$sec.) microseconds.

7. The ultrasonic test block of claim 2 or 3, wherein the distance from the upper surface of the second hole to said second bottom surface segment is traversed by an ultrasonic pulse in one (1 $\mu$sec.) microsecond.

8. The ultrasonic test block of claim 1 or 2, wherein first hole is of larger diameter than said second hole.

9. The ultrasonic test block of claim 2 or 3, wherein said flat end extends to form a leg so as to have a vertical dimension equal to the radius of said arcuate end, thereby prevent wobbling when said calibration block is rested on said first flat bottom segment.

* * * * *